(12) United States Patent
Berner et al.

(10) Patent No.: US 6,540,513 B2
(45) Date of Patent: Apr. 1, 2003

(54) APPARATUS FOR SIMULATING THE AMBIENT COLOR AND TRANSLUCENCE CONDITIONS IN THE ORAL CAVITY OF A PATIENT

(75) Inventors: Markus Berner, Niederhasli (CH); Nicola Pietrobon, Zurich (CH)

(73) Assignee: MHT Optic Research AG, Niederhasli (CH)

( * ) Notice: Subject to any disclaimer, the term of this patent is extended or adjusted under 35 U.S.C. 154(b) by 0 days.

(21) Appl. No.: 09/902,372

(22) Filed: Jul. 10, 2001

(65) Prior Publication Data

US 2002/0015933 A1 Feb. 7, 2002

(30) Foreign Application Priority Data

Jul. 11, 2000 (CH) ................................................ 1361/00

(51) Int. Cl.⁷ ............................................. A61C 19/10
(52) U.S. Cl. ...................................................... 433/26
(58) Field of Search ............................... 433/26, 203.1, 433/29

(56) References Cited

U.S. PATENT DOCUMENTS

| | | | | |
|---|---|---|---|---|
| 2,341,153 A | * | 2/1944 | Meyerson | 433/26 |
| 2,341,154 A | * | 2/1944 | Meyerson | 433/26 |
| 2,341,156 A | * | 2/1944 | Meyerson | 433/26 |
| 2,343,777 A | * | 3/1944 | Lays | 433/26 |
| 2,760,269 A | * | 8/1956 | Adams et al. | 433/26 |
| 4,115,922 A | * | 9/1978 | Alderman | 433/26 |
| 5,904,481 A | * | 5/1999 | Shima | 433/26 |
| 6,038,024 A | | 3/2000 | Brener | 356/326 |

\* cited by examiner

*Primary Examiner*—Cary E. O'Connor
(74) *Attorney, Agent, or Firm*—Maginot, Moore & Bowman

(57) ABSTRACT

The present invention suggests an apparatus for simulating the ambient color and translucence conditions present in the oral cavity of a patient for the purpose of checking the color stimulus specification of dentures prior to their implanting into the oral cavity of a patient. The apparatus comprises an artificial jaw portion including a dimensionally stable, elastic artificial gum body portion simulating at least the vestibulary gum of a patient in which the teeth are inserted. The artificial gum body portion is made of a translucent material. The teeth can be individually replaced by dentures. The color stimulus specification of a denture inserted into the apparatus is checked by means of a color stimulus specification measuring apparatus and compared to the values obtained from a measurement taken in the oral cavity of a patient.

16 Claims, 3 Drawing Sheets

APPARATUS FOR SIMULATING THE AMBIENT COLOR AND TRANSLUCENCE CONDITIONS IN THE ORAL CAVITY OF A PATIENT

BACKGROUND OF THE INVENTION

The present invention refers to an apparatus for simulating the ambient color and translucence conditions present in the oral cavity of a patient for the purpose of checking the color stimulus specification of dentures prior to their implanting into the oral cavity of the patient. Moreover, the invention refers, according to a second aspect, to a method for checking the color stimulus specification of a denture.

PRIOR ART

During the manufacture of dentures, be these crowns, bridges, laminates etc., the problem arises of exactly matching the color of the denture with the color of adjacent teeth. In the meantime, the possibility exists to exactly determine the color of teeth, particularly the color of teeth adjacent to a denture to be implanted. For this purpose, for example a method and an apparatus as disclosed in U.S. Pat. No. 6,038,024 can be adopted; there, a method and an apparatus is described for exactly determining the color stimulus specification of translucent objects, for example teeth and dentures.

However, a problem still remains as far as the quality control during the manufacture of a denture is concerned. Usually, a denture is manufactured by a dental technician in his laboratory. Prior to sending the denture to the dentist who will implant the denture into the oral cavity of the patient, the dental technician should be in a position to check the denture as far as its color, particularly its color stimulus specification, is concerned. Nowadays, such a check is possible only with the help of an existing prefabricated tooth sample, a so-called color key. Thus, in the laboratory of the dental technician, i.e. in the absence of the oral cavity of the patient, it is not possible to perform a direct comparison between the color stimulus of the denture and of the remaining natural teeth of the patient. A possible color mismatch, caused by an erroneous selection of the color key or by a misinterpretation thereof, is recognized only when the dentist implants the denture in the oral cavity of the patient. Of course, this is an absolutely unsatisfactory situation.

Even if the dental technician is in the possession of an apparatus according to U.S. Pat. No. 6,038,024 or a similar apparatus, the denture cannot be checked reliably as far as its color stimulus specification is concerned, since an isolated denture, without the ambience of gum and adjacent teeth, has a different appearance than if it is implanted in the oral cavity of a patient. As soon as the denture is implanted in the oral cavity of the patient, a possible color deviation can be reliably determined if a suitable measuring apparatus is used, but outside of the oral cavity, different, predominantly erroneous measuring results are obtained. The main reason probably is the translucent nature of the tooth material and the color temperature within the oral cavity mainly influenced by the color of the gum; in other words, the ambience greatly influences the color stimulus of a denture.

Thus, since the color of a denture appears correctly only when at least provisionally inserted into the oral cavity of a patient, ideally, the dental technician had to insert the denture first into the oral cavity of the patient to consider whether or not the color still has to be corrected or not; it is understood that, in practice, this is hardly possible.

OBJECTS OF THE INVENTION

Therefore, it is an object of the invention to provide an apparatus for simulating the ambient color and translucence conditions present in the oral cavity of a patient for the purpose of checking the color stimulus specification of dentures prior to their implanting into the oral cavity of the patient, thus enabling the manufacturer of a denture to evaluate the color stimulus specification of a denture under most realistic conditions.

SUMMARY OF THE INVENTION

To meet this and other objects, the present invention provides an apparatus for simulating the ambient color and translucence conditions present in the oral cavity of a patient for the purpose of checking the color stimulus specification of dentures prior to their implanting into the oral cavity of the patient that comprises means for optically simulating body tissue portions and means for optically simulating at least individual teeth. Preferably, the apparatus comprises an artificial jaw portion including a dimensionally stable, elastic artificial gum body portion simulating at least the vestibulary gum of a patient. The means for optically simulating at least individual teeth is inserted into the artificial gum body portion. The artificial gum body portion preferably consists of a translucent material. The means for optically simulating at least individual teeth are individually removable from the artificial gum body portion and replaceable by a denture.

By means of such an apparatus, for the first time, the ambience of the oral cavity of a patient can be simulated as far as color and translucence are concerned to such an extent that the appearance of a denture can be reliably evaluated prior to implanting it into the oral cavity of a patient.

According to another aspect, the invention also provides a method for checking the color stimulus specification of a denture. According to this method, first, the color stimulus specification of a tooth to be replaced or of an adjacent tooth in the oral cavity of a patient is determined and the measured color stimulus specification value is stored as a desired set value. Then, a denture is manufactured, having a color stimulus specification corresponding to that desired set value. This denture is thereafter inserted into an apparatus for simulating the ambient color and translucence conditions present in the oral cavity of a patient for the purpose of checking the color stimulus specification of dentures prior to their implanting into the oral cavity of a patient, as described herein above, and the color stimulus specification of the denture inserted into that simulation apparatus is determined and the measured color stimulus specification value is stored as actual value. Finally, the stored actual value and the stored desired set value are compared and the color of the denture is corrected, if necessary.

BRIER DESCRIPTION OF THE DRAWINGS

In the following, an embodiment of the apparatus according to the invention will be further described, with reference to the accompanying drawings, in which.

DETAILED DESCRIPTION OF A PREFERRED EMBODIMENT OF THE APPARATUS

Figure 1:
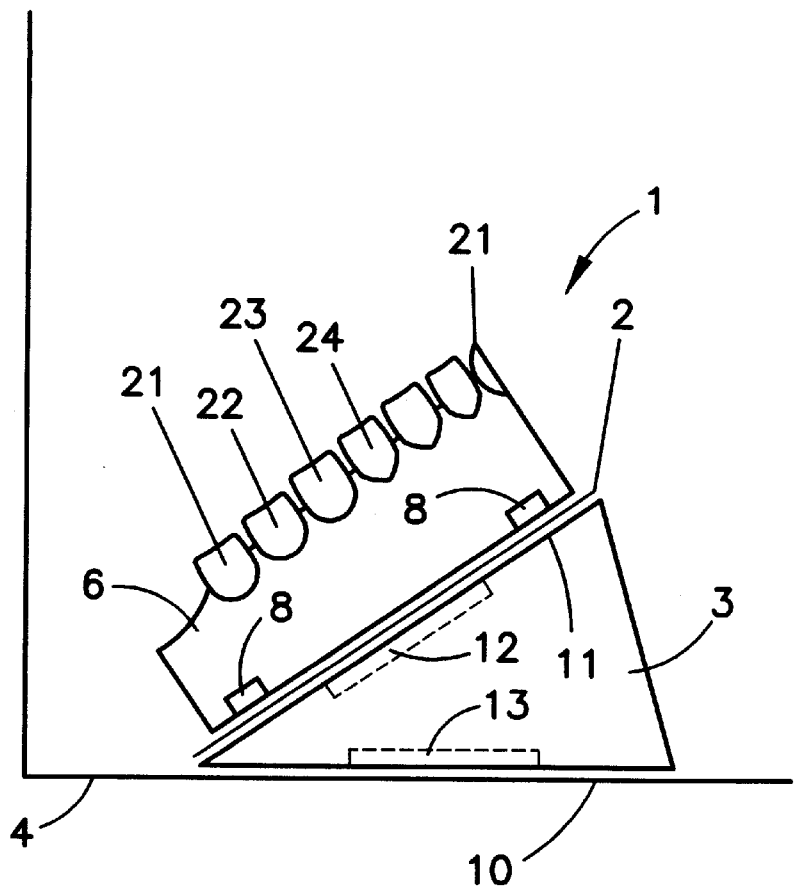
FIG. 1 shows a lateral view of an apparatus for simulating the ambient color and translucence conditions present in the oral cavity of a patient.

The general design of the apparatus for simulating the ambient color and translucence conditions present in the oral cavity of a patient shall be further explained with reference to FIG. 1. The apparatus comprises an artificial jaw portion 1, a base plate member 2, a pedestal 3 and a stand 4. The stand 4 comprises a rectangularly bent sheet metal piece made of a ferro-magnetic material, preferably steel, and is painted black. The artificial jaw portion 1 comprises a dimensionally stable, but elastic artificial gum body member 6 in which the teeth Z1, Z2, Z3 etc. are inserted. The artificial gum body member 6 is made of a translucent material and simulates the vestibulary gum.

The artificial gum body member 6 comprises a plurality of magnest 8 inserted therein at that side facing the pedestal 3; thus, the artificial gum body member 6 adheres to the base plate member 2. The pedestal itself comprises two lateral faces 10, 11 enclosing an acute angle, whereby each of the lateral faces 10 and 11 is provided with a magnet 12 and 13, respectively. Thus, the one lateral face 10 of the pedestal 3 adheres to the stand 4 and the other lateral face 11 of the pedestal 3 adheres to the base plate 2.

Figure 2:
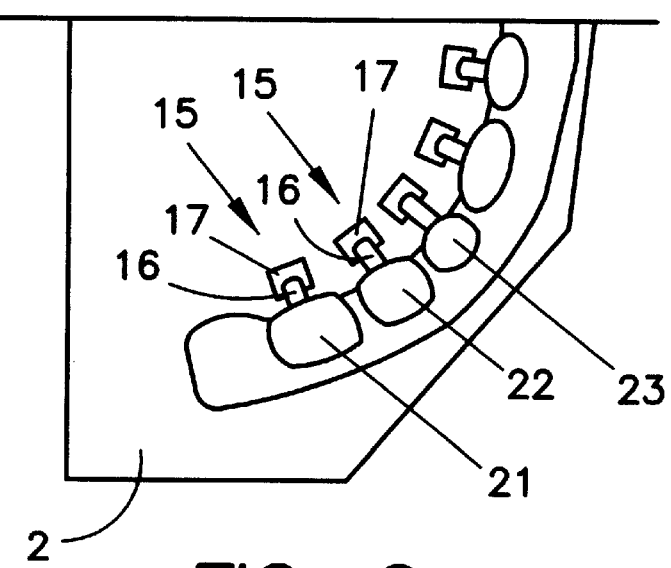
FIG. 2 shows a top view of a partially illustrated jaw portion.
Figure 3:
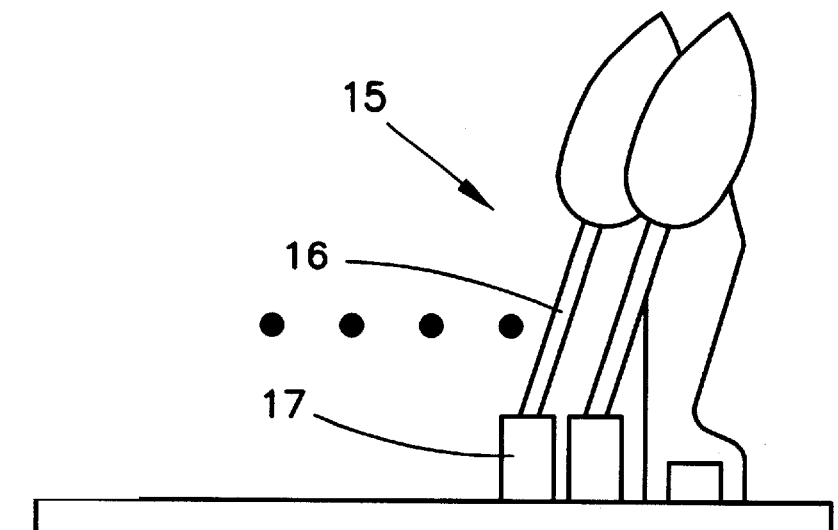
FIG. 3 shows a cross sectional view of a jaw portion.

As can be seen in FIGS. 2 and 3, the individual teeth Z1, Z2, Z3 are mounted on holders 15 consisting of a shaft member 16 and a magnet 17 fixed to the end of the shaft member 16; thereby, the magnets ensure that the particular tooth adheres to the base plate member 2. The inner side of the artificial gum body member 6 is provided with (not shown) recesses for receiving and guiding the above-mentioned shafts 16 of the teeth Z1, Z2, Z3. By virtue of this design, the individual teeth Z1, Z2, Z3 can be individually removed, inserted, displaced and re-inserted at any time. Once one of the teeth Z1, Z2, Z3 has been removed, a denture can be inserted in its place.

Figure 4:
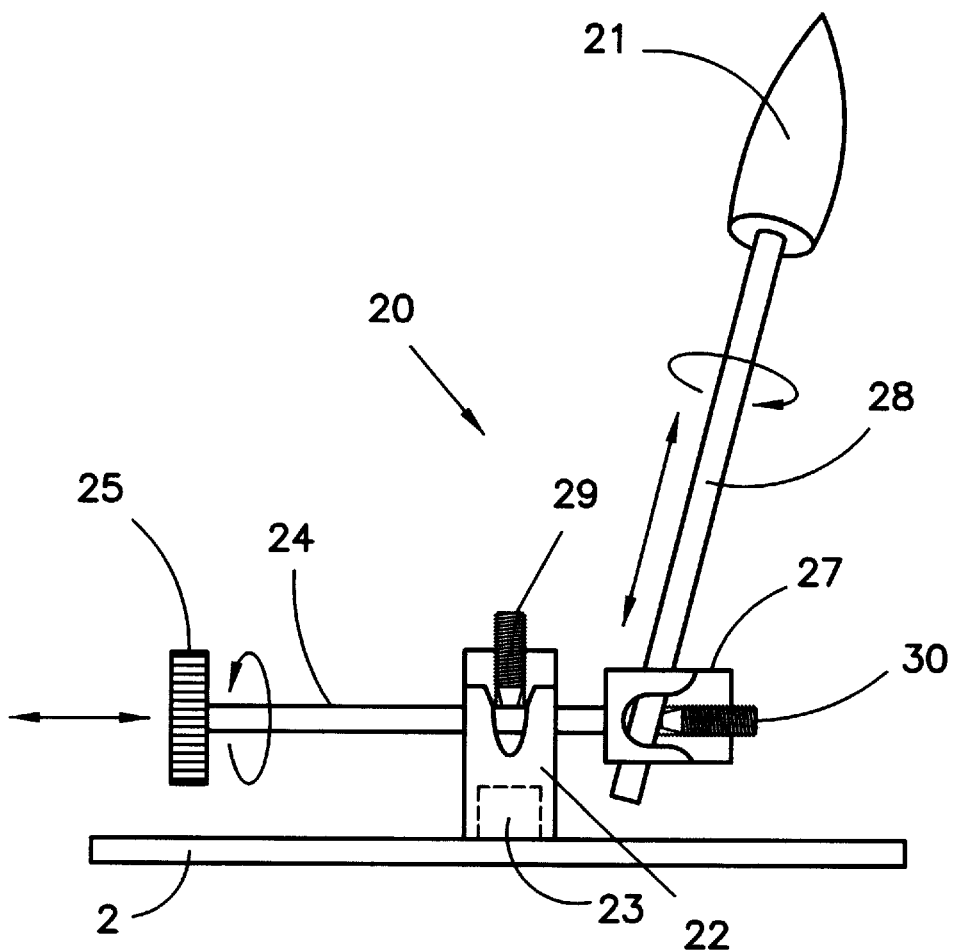
FIG. 4 shows a lateral view of a holding assembly for fixing and positioning a denture.

For fixing the dentures, a fixing assembly 20 according to and as shown in FIG. 4 is provided that ensures an exact positioning of the denture 21 in the artificial gum body member 6. The fixing assembly 20 comprises a holder 22 provided with a magnet 23 ensuring an adhering thereof to the base plate member 2. In this holder 22, a first essentially horizontally running shaft member 24 is received in such a way that it is rotatable and longitudinally movable. One end of the first shaft member 24 is provided with a knurled knob 25, enabling the first shaft member 24 to be manually rotated. The other end of the first shaft member 24 is provided with a locking device 27 in which a second essentially vertically running shaft member 28 is received in such a way that it is rotatable and longitudinally movable. The denture 21 can be attached to the free end of that second shaft member 28. Thereby, the denture 21 can be clamped to the end of the shaft member 28 or fixed thereto by means of a suitable adhesion wax. Both the holder 22 and the locking device 27 each are provided with a set screw 29 and 30, respectively, for locking the particular shaft member 24 and 28, respectively, in the desired position.

It is understood that not only a denture representing a single tooth can be attached to the shaft member 28 and inserted into the artificial gum body member 6 by means of the fixing assembly 20, but also a denture comprising of a plurality of teeth, a so-called bridge. Since it is required, in such a case, to differentiate the radius of the arc-shaped denture, the radius of the artificial gum body member 6 can be increased or decreased accordingly. This is made possible by manufacturing the artificial gum body member of a flexible material simulating but the vestibulary gum situation and adaptable to the desired radius, since the magnets 8 fix the artificial gum body member 6 to the base plate 2 in practically any desired shape (cf. FIG. 1).

Preferably, both a plurality of sets of teeth Z1, Z2, Z3 etc. slightly differing in color and a plurality of sets of artificial gum body members 6 also slightly differing in color are provided that can be combined in any desired way in order to simulate the optical situation in the oral cavity of the patient in a optimal way. According to FIG. 1, the lower jaws are simulated by the artificial jaw portion 1. However, if one rotates the artificial jaw portion 1 together with the pedestal 3 by 180° and fixes them to the vertical leg of the stand 4, the upper jaws can be simulated by means of the same artificial jaw portion 1.

Figure 5:
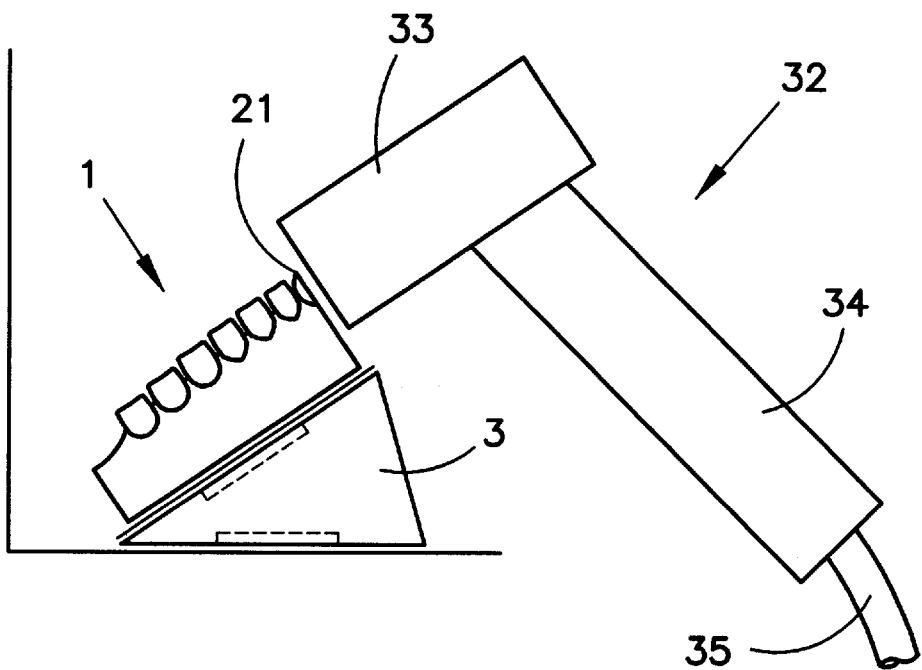
FIG. 5 shows the apparatus of FIG. 1, together with an apparatus for measuring the color stimulus specification of a denture to be inserted into the lower jaws of a patient.

FIG. 5 shows the apparatus of FIG. 1 together with an apparatus 32 for measuring the color stimulus specification of a denture in comparison to a desired color stimulus specification previously measured in the oral cavity of a patient. It is understood that the apparatus 32 is shown in a very simplified manner; i.e., only the probe head 33 and the handle 34 are shown. Via the cable 35, the apparatus 32 can be connected to an analyzing device, for example a computer; it is understood that such analyzing device is not shown in the drawings. The probe head 33 is provided with an illumination device as well as with an optical receiving device for capturing the light reflected by the measuring object under test. Preferably, the illumination device or the optical receiving device comprises a color separator, separating visible light into different wave length portions. Moreover, preferably a monitor is also provided for visualizing the measurement date captured by the optical receiving device. Regarding further details about the design and operation of such an apparatus 32 for measuring the color stimulus specification of a denture, reference is made to U.S. Pat. No. 6,038,024, assigned to MHT Optic Research, Niederhasli, Switzerland.

Figure 6:
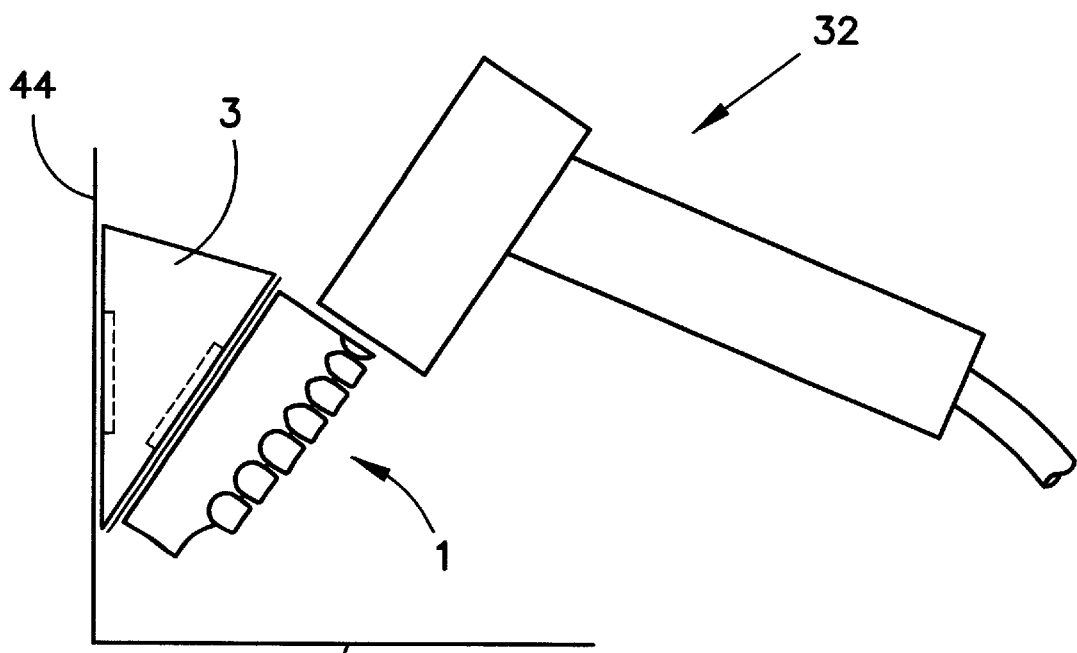
FIG. 6 shows the apparatus of FIG. 1, together with an apparatus for measuring the color stimulus specification of a denture to be inserted into the upper jaws of a patient.

While in the illustration of FIG. 5 the lower jaws are simulated by means of the artificial jaw portion 1, the same artificial jaw portion 1 is used to simulate the upper jaws, as shown in FIG. 6. For this purpose, the artificial jaw portion 1, together with the pedestal 3, has been rotated by 180° and fixed to the vertical leg 4a of the stand 4. It is understood that also two separate artificial jaw portions can be provided, whereby one simulates the lower jaws and the other one the upper jaws.

The course of operation for checking the color stimulus specification of a denture prior to implanting it into the oral cavity of a patient is as follows:

The dentist, eventually even the dental technician manufacturing the denture, determines the color of the teeth of the patient. Ideally, this is accomplished by means of an apparatus for determining the color stimulus specification as disclosed in U.S. Pat. No. 6,038,024. Thereafter, the dentists sends the measurement date, e.g. by e-mail, to the dental technician. In line with these specifications, the dental technician manufactures the denture. Now the dental technician inserts the denture into the apparatus according to the invention and, for example, as shown in FIG. 1 and determines the color stimulus specification by means of the apparatus 32 as shown in FIGS. 5 and 6. After that measurement, he calculates the difference between the obtained measurement values and the specifications determined in the oral cavity of the patient. If this difference is within acceptable limits (e.g. CIE-Lab dE≦2.0), the color of the denture is in order; if not, the color of the denture must be corrected or the denture has to be manufactured again.

If the patient wishes to get a different color than the color of his natural teeth, it can be determined by the dentist or the dental technician in cooperation with the patient by means of the commercially available so-called color keys. Now, the dental technician can perform a color quality control of the manufactured denture by means of the apparatus as described herein before by comparing the color stimulus specifications of the denture with the stored data of the color key. Shouldn't the data of the color key not be available in the color stimulus specifications measuring apparatus, the dental technician can scan the corresponding sample of the color stimulus specification of the color key and perform the color quality control on the basis of these data.

If the dentist has transmitted the measurement data via e-mail to the dental technician, the latter one can use these data as desired specification data. However, if the dental technician makes use of a computer as an analyzing device, he can store the desired color specification directly in the computer, and he can compare the measurement data taken on the natural tooth to the measurement data obtained with the denture. Preferably, such comparison is not made with the finished denture, but with the pre-manufactured blank denture. In this case, possible color deviations can be easily corrected. The whole operation makes sense particularly in that case if the apparatus according to the invention is used together with an apparatus for determining the color stimulus specification of a tooth and a denture, respectively, which illuminates the tooth to be measured and the denture, respectively, as well as the ambience (adjacent teeth, gum) more or less homogeneously.

What is claimed is:

1. An apparatus for simulating the ambient color and translucence conditions present in the oral cavity of a patient for the purpose of checking the color stimulus specification of dentures prior to their implanting into the oral cavity of a patient, comprising means for optically simulating body tissue portions and means for optically simulating at least individual teeth, and further comprising an artificial jaw portion including a dimensionally stable, elastic artificial gum body portion simulating at least the vestibulary gum of a patient, said means for optically simulating at least individual teeth being inserted into said artificial gum body portion, said artificial gum body portion consisting of a translucent material, and said means for optically simulating at least individual teeth being individually removable from said artificial gum body portion and replaceable by a denture, and further comprising a base plate made of a ferromagnetic material, said artificial gum body portion being provided with a first magnet and adapted to be attached to said base plate, and said means for optically simulating at least individual teeth comprising a holder provided with a second magnet for attaching said means for optically simulating at least individual teeth to said base plate.

2. An apparatus according to claim 1, comprising a plurality of teeth that can be individually removed and replaced by a denture to be checked regarding its color stimulus specification.

3. An apparatus according to claim 1 in which said means for optically simulating at least individual teeth comprises a plurality of sets of teeth having different colors.

4. An apparatus according to claim 1 in which said means for optically simulating body tissue portions comprises a plurality of dimensionally stable, elastic artificial gum body portions having different colors.

5. An apparatus for simulating the ambient color and translucence conditions present in the oral cavity of a patient for the purpose of checking the color stimulus specification of dentures prior to their implanting into the oral cavity of a patient, comprising means for optically simulating body tissue portions and means for optically simulating at least individual teeth, and further comprising an artificial jaw portion including a dimensionally stable, elastic artificial gum body portion simulating at least the vestibulary gum of a patient, said means for optically simulating at least individual teeth being inserted into said artificial gum body portion, said artificial gum body portion consisting of a translucent material, and said means for optically simulating at least individual teeth being individually removable from said artificial gum body portion and replaceable by a denture and further comprising a fixing assembly adapted to fix and position said denture in said artificial gum body portion.

6. An apparatus according to claim 1 in which said fixing assembly is adapted to be attached to said base plate and comprises an adjustable shaft to which said denture can be fixed.

7. An apparatus according to claim 1 in which the inner side of said artificial gum body portion is provided with recesses adapted to receive a shaft provided on said holder and said fixing assembly, respectively.

8. An apparatus according to claim 5 in which said dimensionally stable, elastic artificial gum body portion is flexible and can be formed into different shapes.

9. An apparatus for simulating the ambient color and translucence conditions present in the oral cavity of a patient for the purpose of checking the color stimulus specification of dentures prior to their implanting into the oral cavity of a patient, comprising means for optically simulating body tissue portions and means for optically simulating at least individual teeth, and further comprising an artificial jaw portion including a dimensionally stable, elastic artificial gum body portion simulating at least the vestibulary gum of a patient, said means for optically simulating at least individual teeth being inserted into said artificial gum body portion, said artificial gum body portion consisting of a translucent material, and said means for optically simulating at least individual teeth being individually removable from said artificial gum body portion and replaceable by a denture and further comprising a black stand in the shape of a rectangularly bent sheet metal to which said artificial jaw portion can be fixed.

10. An apparatus according to claim 9, further comprising a pedestal provided with two lateral faces enclosing an acute angle, each of said lateral faces being provided with a magnet such that one of said lateral faces of said pedestal can be attached to said stand and another of said lateral faces to said base plate.

11. An apparatus for simulating the ambient color and translucence conditions present in the oral cavity of a patient for the purpose of checking the color stimulus specification of dentures prior to their implanting into the oral cavity of a patient, comprising:

means for optically simulating at least individual teeth;

an artificial jaw portion including a dimensionally stable, elastic artificial gum body portion simulating at least the vestibulary gum of a patient;

means for determining the color stimulus specification of a denture inserted into said artificial jaw portion and for comparing said determined color stimulus specification with a color stimulus specification measured in the oral cavity of a patient;

said means for optically simulating at least individual teeth being inserted into said artificial gum body portion;

said artificial gum body portion consisting of a translucent material; and said means for optically simulating at least individual teeth being individually removable from said artificial gum body portion and replaceable by said denture.

12. An apparatus according to claim 11 in which said means for determining the color stimulus specification of a denture comprises:

an illumination means for illuminating said denture as well as regions adjacent to said denture;

at least one optical detection assembly for receiving the light reflected by said denture illuminated by said illumination means; and analyzing means for analyzing the measurement data provided by said detection assembly.

13. An apparatus according to claim 12 in which said illumination means or said detection assembly includes a color separator adapted to separate visible light into different wave length portions.

14. An apparatus according to claim 12, in which said detection assembly includes a lens assembly and at least one image sensor, and being adapted to deliver output signal data in response to the captured light, whereby a probe head is provided and adapted to receive selected parts and elements of said detection assembly, said probe head being adapted to be displaced towards said object under test for taking a measurement, and whereby means for visualizing said output signal data delivered by said detection assembly are provided.

15. A method of checking the color stimulus specification of a denture, comprising the steps of:

determining the color stimulus specification of a tooth to be replaced or of an adjacent tooth in the oral cavity of a patient;

storing the measured color stimulus specification value as a desired set value;

manufacturing a denture having a color stimulus specification corresponding to said desired set value;

inserting said denture into an apparatus for simulating the ambient color and translucence conditions present in the oral cavity of a patient for the purpose of checking the color stimulus specification of dentures prior to their implanting into the oral cavity of a patient, comprising means for optically simulating body tissue portions and means for optically simulating at least individual teeth;

determining the color stimulus specification of said denture inserted into said apparatus for simulating the ambient color and translucence conditions present in the oral cavity of a patient and storing the measured color stimulus specification value as an actual value; and comparing said actual value and said desired set value.

16. A method according to claim 15 in which, during said step of determining the color stimulus specification of said denture inserted into said apparatus for simulating the ambient color and translucence conditions present in the oral cavity of a patient, both the denture and adjacent teeth are homogeneously illuminated.

\* \* \* \* \*